(12) United States Patent
Channer et al.

(10) Patent No.: US 7,544,169 B2
(45) Date of Patent: Jun. 9, 2009

(54) BLOOD COLLECTION DEVICE

(75) Inventors: Don Channer, Main Beach (AU); Aaron Rodd, Burleigh Waters (AU)

(73) Assignee: Medigard Limited (AU)

( * ) Notice: Subject to any disclaimer, the term of this patent is extended or adjusted under 35 U.S.C. 154(b) by 0 days.

(21) Appl. No.: 10/587,139

(22) PCT Filed: Jan. 21, 2005

(86) PCT No.: PCT/AU2005/000063

§ 371 (c)(1), (2), (4) Date: Apr. 5, 2007

(87) PCT Pub. No.: WO2005/070292

PCT Pub. Date: Aug. 4, 2005

(65) Prior Publication Data

US 2007/0265549 A1    Nov. 15, 2007

(30) Foreign Application Priority Data

Jan. 23, 2004    (AU) .............................. 2004900310

(51) Int. Cl.
*A61B 5/00*    (2006.01)
*A65D 81/00*    (2006.01)

(52) U.S. Cl. ................. 600/576; 600/573; 600/574; 600/575; 600/577; 600/578; 600/579; 604/110; 604/195; 604/198

(58) Field of Classification Search ................. 600/582, 600/573–579; 606/110, 195, 198
See application file for complete search history.

(56) References Cited

U.S. PATENT DOCUMENTS

| | | | |
|---|---|---|---|
| 5,000,736 A | * | 3/1991 | Kaufhold et al. ............ 604/110 |
| 5,057,079 A | | 10/1991 | Tiemann et al. |
| 5,057,087 A | | 10/1991 | Harmon |
| 5,067,490 A | | 11/1991 | Haber |
| 5,070,884 A | | 12/1991 | Columbus et al. |
| 5,070,885 A | | 12/1991 | Bonaldo |
| 5,084,029 A | | 1/1992 | Nacci et al. |
| 5,125,898 A | | 6/1992 | Kaufhold, Jr. et al. |

(Continued)

FOREIGN PATENT DOCUMENTS

WO    WO 1999/023947    5/1999

*Primary Examiner*—Max Hindenburg
*Assistant Examiner*—Sean P Dougherty
(74) *Attorney, Agent, or Firm*—Cantor Colburn LLP (57) ABSTRACT

A blood collection device comprises an open ended syringe like housing into which a vacutainer can be inserted. The front of the device contains a needle holder and a double ended needle. The needle holder is attached to the device in a special manner that enables the needle holder to be decoupled and retracted into the device but only after the vacutainer has been removed and a separate needle retraction device has been inserted into the open end of the housing and pushed against the inner end of the needle holder. The needle retraction device comprises a hollow body which is under vacuum and which has an open end closed by a piston. The piston is of a special design that functions to decouple the needle holder from the blood collection device and to lock to the needle holder and at the same time to be decoupled from the hollow body the result of which is that the piston containing the needle holder and the attached contaminated needle is sucked back into the hollow body to render the needle safe.

9 Claims, 8 Drawing Sheets

U.S. PATENT DOCUMENTS

| | | |
|---|---|---|
| 5,176,640 A | 1/1993 | Nacci et al. |
| 5,180,370 A | 1/1993 | Gillespie |
| 5,193,552 A | 3/1993 | Columbus et al. |
| 5,209,739 A | 5/1993 | Talalay |
| 5,215,533 A | 6/1993 | Robb |
| 5,254,100 A | 10/1993 | Huband |
| 5,263,934 A | 11/1993 | van den Haak |
| 5,318,538 A | 6/1994 | Martin |
| 5,346,475 A | 9/1994 | Gregorio |
| 5,352,203 A * | 10/1994 | Vallelunga et al. .......... 604/110 |
| 5,423,758 A | 6/1995 | Shaw |
| 5,498,244 A | 3/1996 | Eck |
| 5,520,649 A | 5/1996 | Novacek et al. |
| 5,531,694 A | 7/1996 | Clemens et al. |
| 5,542,927 A | 8/1996 | Thorne et al. |
| 5,562,103 A | 10/1996 | Sak |
| 5,562,625 A | 10/1996 | Stefancin et al. |
| 5,578,015 A | 11/1996 | Robb |
| 5,658,257 A | 8/1997 | Ryles |
| 5,820,605 A | 10/1998 | Zdeb et al. |
| 5,868,713 A | 2/1999 | Klippenstein |
| 5,891,104 A | 4/1999 | Shonfeld et al. |
| 6,004,278 A | 12/1999 | Botich et al. |
| 6,066,115 A | 5/2000 | Chang Lai et al. |
| 6,077,245 A | 6/2000 | Heinrich et al. |
| 6,132,401 A | 10/2000 | Van Der Meyden |
| 6,186,960 B1 * | 2/2001 | Tripp et al. .................. 600/576 |
| 6,193,695 B1 | 2/2001 | Rippstein, Jr. et al. |
| 6,210,375 B1 | 4/2001 | Moulton et al. |
| 6,409,704 B1 | 6/2002 | Tsai |
| 6,413,236 B1 | 7/2002 | Van Dyke |
| 6,471,677 B2 | 10/2002 | Domici, Jr. |
| 6,512,565 B1 | 1/2003 | Lee et al. |
| 6,537,257 B1 | 3/2003 | Wien |
| 6,572,565 B2 * | 6/2003 | Daley et al. .................. 600/573 |
| 6,706,019 B1 | 3/2004 | Parker et al. |
| 6,743,199 B2 | 6/2004 | Shue et al. |
| 6,846,301 B2 | 1/2005 | Smith et al. |
| 6,911,018 B2 | 6/2005 | Gordon |
| 6,918,889 B1 | 7/2005 | Brunel |
| 6,921,386 B2 | 7/2005 | Shue et al. |
| 6,994,690 B2 | 2/2006 | Kiehne et al. |
| 7,329,238 B2 | 2/2008 | Halseth et al. |
| 7,381,199 B2 | 6/2008 | Kuan |
| 2002/0055719 A1 | 5/2002 | Lo |
| 2002/0173750 A1 | 11/2002 | Huang et al. |
| 2002/0193736 A1 | 12/2002 | Kiehne |
| 2003/0069518 A1 | 4/2003 | Daley et al. |
| 2003/0212371 A1 | 11/2003 | Smith et al. |
| 2004/0087907 A1 | 5/2004 | Smith et al. |
| 2004/0092884 A1 | 5/2004 | Rimlinger et al. |
| 2004/0106903 A1 | 6/2004 | Shue et al. |
| 2004/0153035 A1 | 8/2004 | Shih |
| 2004/0210198 A1 | 10/2004 | Shih |
| 2004/0225263 A1 | 11/2004 | Chen |
| 2004/0254530 A1 | 12/2004 | Chou et al. |
| 2005/0080380 A1 | 4/2005 | Hsieh et al. |
| 2005/0192533 A1 | 9/2005 | Lo |
| 2005/0203458 A1 | 9/2005 | Shih |
| 2006/0084918 A1 | 4/2006 | Lou |
| 2006/0100577 A1 | 5/2006 | Shue et al. |
| 2006/0106340 A1 | 5/2006 | Goossens et al. |
| 2006/0106341 A1 | 5/2006 | Lou |
| 2006/0111671 A1 | 5/2006 | Klippenstein |
| 2006/0167409 A1 | 7/2006 | Pelkey et al. |
| 2006/0167412 A1 | 7/2006 | Marshall |
| 2006/0173411 A1 | 8/2006 | Barere |
| 2006/0229555 A1 | 10/2006 | Wu |
| 2006/0235354 A1 | 10/2006 | Kaal et al. |
| 2006/0253074 A1 | 11/2006 | Thayer et al. |
| 2007/0005015 A1 | 1/2007 | Shue et al. |
| 2007/0060886 A1 | 3/2007 | Knepshield |
| 2007/0185447 A1 | 8/2007 | Lu |
| 2007/0250004 A1 | 10/2007 | Tung |
| 2007/0255212 A1 | 11/2007 | Smith et al. |
| 2007/0265549 A1 | 11/2007 | Channer et al. |
| 2008/0033355 A1 | 2/2008 | Mazzara |
| 2008/0045899 A1 | 2/2008 | Wu |
| 2008/0097303 A1 | 4/2008 | Chen et al. |
| 2008/0097305 A1 | 4/2008 | Tsai |
| 2008/0097308 A1 | 4/2008 | Schiller et al. |
| 2008/0119786 A1 | 5/2008 | Stewart et al. |
| 2008/0132837 A1 | 6/2008 | Lin |
| 2008/0154193 A1 | 6/2008 | Chang |
| 2008/0154194 A1 | 6/2008 | Huang |
| 2008/0154195 A1 | 6/2008 | Huang |
| 2008/0161760 A1 | 7/2008 | Channer |
| 2008/0177229 A1 | 7/2008 | Suresh et al. |
| 2008/0215000 A1 | 9/2008 | Barere |
| 2008/0243073 A1 | 10/2008 | Liu |
| 2008/0255513 A1 | 10/2008 | Kaal |

* cited by examiner

BLOOD COLLECTION DEVICE

FIELD OF THE INVENTION

This invention is directed to a blood collecting device which has a needle, a housing, which uses a vacuum tube to collect the blood, and where the needle can be retracted after use in such a manner that needlestick injury is reduced or eliminated. The invention will be described with reference to its use to collect blood, but it should be appreciated that the device may also be used to collect other types of body fluids.

BACKGROUND ART

It is very well-known and standard practice to collect blood from a patient using a device commonly known as a "vacutainer". This type of known device has a double ended needle which is fitted to a housing. The housing approximates a shortened syringe barrel. The double ended needle is fitted to the housing such that a longer part of the needle extends from the housing and a shorter part of the needle extends into the housing. To take blood from a patient, the longer part of the needle is inserted into a blood vessel. The blood is collected into a container which approximates a test tube and which can be made of glass or plastic. The container has an open end which is covered by a rubber stopper (or stopper made of other material), and the container is partially evacuated. The container is pushed up into the housing until such time as the inner end of the needle pieces the rubber stopper. The partial vacuum in the container causes blood to be sucked through the needle and into the container. When the blood collection is completed, the container is removed from the housing. The housing containing the attached needle is then pulled back to remove the needle from the blood vessel. The housing containing the attached needle then needs to be disposed of in a safe manner but it is at this point that needlestick injury can occur as the needle is (a) contaminated and the needle (b) projects from the front of the housing.

Therefore, there would be an advantage if it were possible to have a blood collecting device which still uses the above principle of a partially evacuated container, but which has some form of mechanism to enable the needle to be retracted to reduce or even to the eliminate the possibility of needlestick injury.

It will be clearly understood that, if a prior art publication is referred to herein, this reference does not constitute an admission that the publication forms part of the common general knowledge in the art in Australia or in any other country.

BRIEF SUMMARY OF THE INVENTION

It is an object of the invention to provide a blood collection device that may overcome or reduce the possibility of needlestick injury.

In one form, the invention resides in a blood collection device comprising a housing, a needle holder, a needle which is double ended and has a first end (outer end) that projects from the housing and a second end (inner end) that projects into the housing, the needle holder being releasably attached relative to the housing to enable the needle holder and the attached needle to be retracted.

In another form, the invention resides in a blood collection device assembly comprising a blood collection device as described above, and a needle retraction device, the needle retraction device able to be pushed into the housing to release the needle holder from the housing and to retract the needle holder containing the attached needle into the needle retraction device.

In this manner, blood can be collected in a manner not dissimilar to the "vacutainer" technique. However, once the required volume of blood has been collected, instead of simply pulling the needle out of the blood vessel and having a contaminated projecting needle which creates a sharps risk, a needle retraction device is pushed into the housing and towards the end of the housing which functions to decouple the needle holder (containing the contaminated needle) from the housing and then retracts the needle into the needle retraction device which functions to protect the needle against needlestick injury. It is considered that this technique will be much safer and very easy to use, and there is very little likelihood that the contaminated needle can be touched.

The blood collection device comprises the housing, a needle holder and a needle which is generally well-known. However, as part of the present invention, the needle holder is releasably attached relative to the housing to enable the needle holder to be retracted into a separate needle retraction device.

The housing will typically comprise an elongate cylindrical hollow body into which a blood collecting container can pass. The body will typically have an open rear end to enable the blood collecting container to be pushed into the housing. The front of the housing will typically have a configuration to enable the needle holder to be attached to the front of the housing. Typically, the front of the housing will have a smaller diameter extending collar. The collar may be provided with engagement means to enable the needle holder to be releasably attached relative to the collar. The engagement means may comprise a recess. The recess may be an annular recess. It is envisaged that a plurality of recesses may be provided or that the recess is a single recess or a plurality of recesses. The recess may comprise a small groove extending along the inner wall of the collar. Alternatively, the engagement means may comprise a projection or a plurality of projections.

The needle holder will typically be provided with an internal passageway to accommodate the steel needle. Suitably, the needle holder is provided with engagement means to engage with the housing and particularly to engage with the collar. If the engagement means on the collar comprises a recess, the engagement means on the needle holder will typically comprise a projection that can engage with the recess to hold the needle holder to the collar and therefore to the housing. However, if the engagement means on the collar comprises a projection, the engagement means on the needle holder will typically comprise a recess. It is envisaged that the engagement means on the needle holder may comprise a plurality of projections, a plurality of recesses, or a combination thereof. Typically however, the engagement means on the needle holder will comprise a projection and will typically comprise a small annular rib that can engage into the small annular recess on the collar.

The needle holder may be formed from separate parts and will typically be formed from two parts being a larger internal part and a smaller external part. The internal part may be provided with the passageway to accommodate the steel needle and can be seen as the "main body" of the needle holder. The external part may extend about the main body or at least partially about the main body and will typically be provided with the engagement means. The external part and the internal part can be attached together by any suitable means.

The needle may be a conventional blood collecting needle which is well-known in the art.

The blood collecting containers that are used to collect blood may be of conventional design and these will typically comprise an elongate hollow body which is partially evacuated and which is provided with a pierceable front stopper. As the container is pushed through the housing, the inner part of the needle will pierce the front stopper and the partial vacuum in the container will cause blood to be sucked through the needle and into the container. This arrangement is well-known.

The needle retraction device will typically be a separate part which is inserted into the housing only after sufficient blood has been collected in the blood collecting containers, and it is now desirable to retract the needle in a safe manner. The needle retraction device will typically comprise an elongate body that can be at least partially pushed into the housing. The elongate body may therefore be substantially tubular. The elongate body will typically have an evacuated chamber in the body, and the function of the chamber will be to accommodate the needle and the needle holder in a safe manner.

The evacuated chamber will typically have an open front end which is plugged with a plug. The plug will typically be slideable along the chamber and in a sealing manner and therefore the plug may be provided with sealing means to enable the plug to be sealed on the inside wall of the evacuated chamber but still able to slide along the evacuated chamber. The sealing means may comprise sealing rings. The plug may itself be provided with an internal chamber, and the internal chamber may function to accommodate the part of the needle that extends inside the housing. This internal chamber does not need to be evacuated. If desired, the front of the plug may have a pierceable or frangible wall.

The plug is releasably attached relative to the body of the needle retraction device to prevent the plug from being sucked back into the partially evacuated chamber. Typically, the plug will contain a releasable engagement means which may comprise a resilient member or portion which attaches to the body. However, upon movement of the engagement means to the free position, the plug will now be released from the body and will be sucked back into the partially evacuated chamber.

The construction and arrangement of the needle retraction device and particularly the front part of the needle retraction device is such that when the device is pushed into the housing and against the inner end of the housing, the plug and typically the engagement means on the plug will couple to the needle holder and this coupling motion will also release the needle holder from the housing. As well, this coupling motion will also release the plug from the body of the needle retraction device. Thus, the plug will be sucked back into the evacuated chamber, and as the plug is attached to the needle holder, will also cause the needle holder to be sucked back into the chamber.

Suitably, a locking means is provided to lock the needle retraction device in the housing once the needle has been sucked into the needle retraction device. The locking means may function to prevent the needle retraction device from being withdrawn from the housing. The entire assembly can then be disposed of in a safe manner.

BRIEF DESCRIPTION OF THE DRAWINGS

Two embodiments of the invention will be described with reference to the following drawings in which.

BEST MODE

Figure 9:
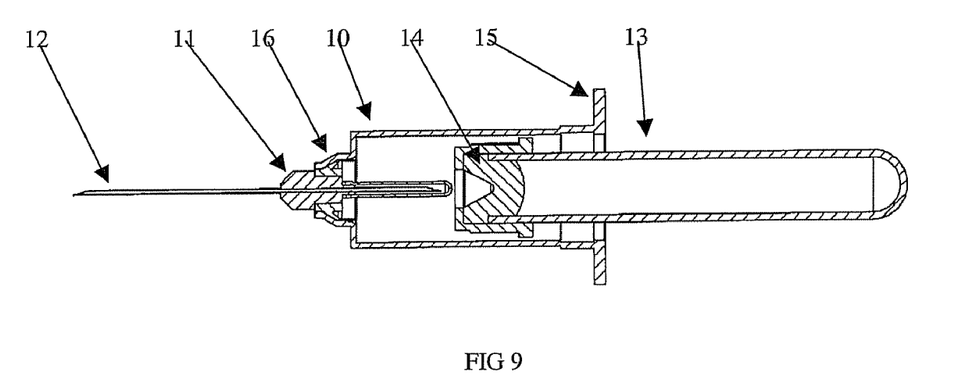
FIG. 9 illustrates a blood collection device according to a second embodiment of the invention together with a conventional blood collecting chamber which is partially pushed into the housing.
Figure 10:
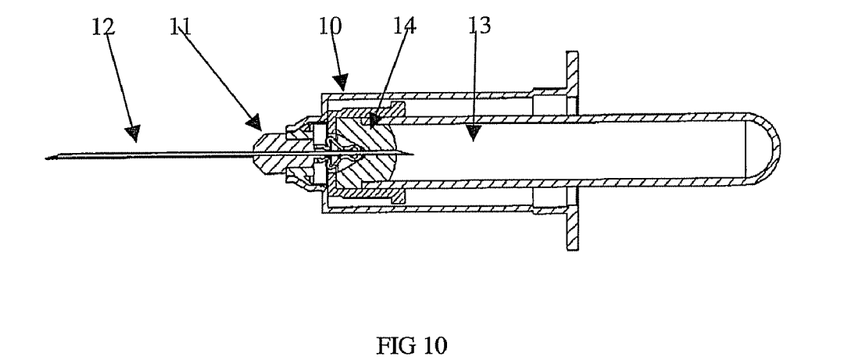
FIG. 10 illustrates the device of FIG. 9 but this time with the conventional blood collecting chamber being pushed fully into the housing to enable blood to be sucked into the chamber.

Referring to the drawings and initially to the second embodiment illustrated in FIGS. 9-18, and specifically to FIGS. 9 and 10 there is illustrated a blood collection device according to an embodiment of the invention. Basically, the blood collection device comprises three main portions being a housing 10, a needle holder 11 and a double ended needle 12. Also illustrated in these figures is a blood collection chamber 13 which is of conventional design and which comprises a partially evacuated chamber body which is sealed with a forward plug 14 which can be pierced by the inner part of needle 12.

Housing 10 is tubular in configuration and will typically be made of plastics material and has a rear portion provided with an outwardly extending flange 15, the flange functioning to assist with a one-handed operation of the needle retraction device that will be described in greater detail below. Flange 15 however is quite similar to the flanges on syringes. Housing 10 is entirely hollow to enable chamber 13 to pass into the housing and towards the inner end of needle 12.

Figure 14:
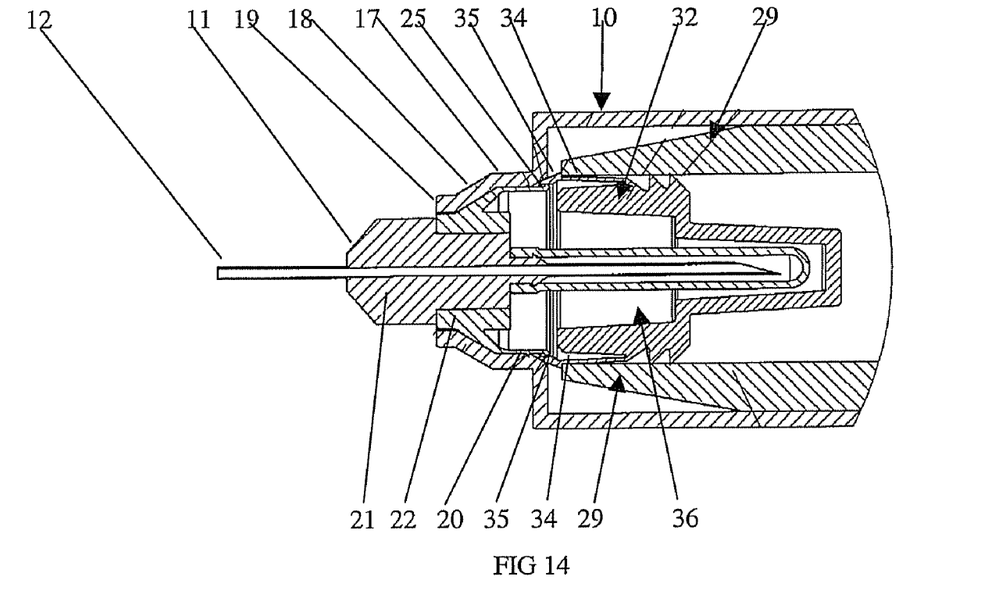
FIG. 14 illustrates in greater detail the initial process of decoupling the needle holder from the housing and decoupling the plug from the needle retraction device.
Figure 15:
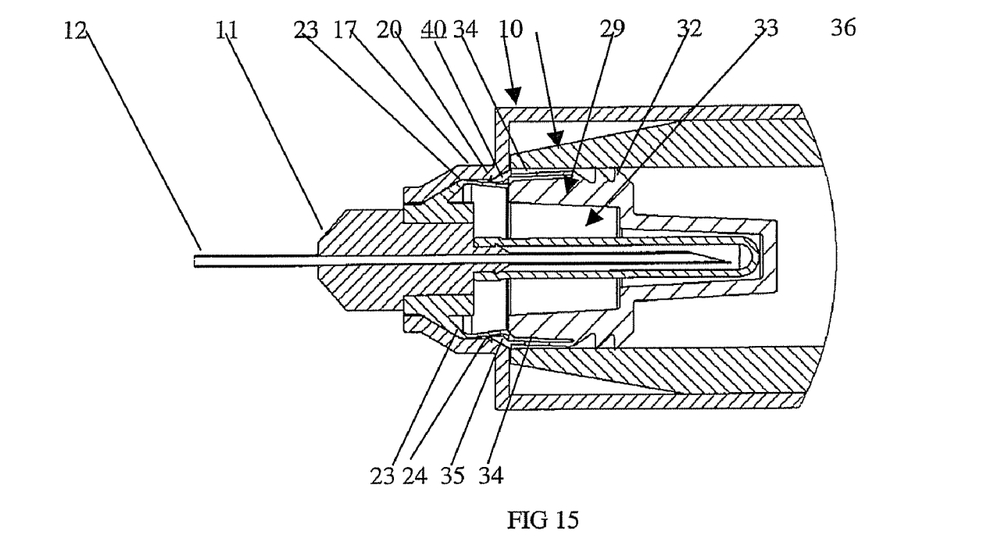
FIG. 15 illustrates in greater detail the final process of decoupling the needle holder from the housing and decoupling the plug from the needle retraction device.
Figure 16:
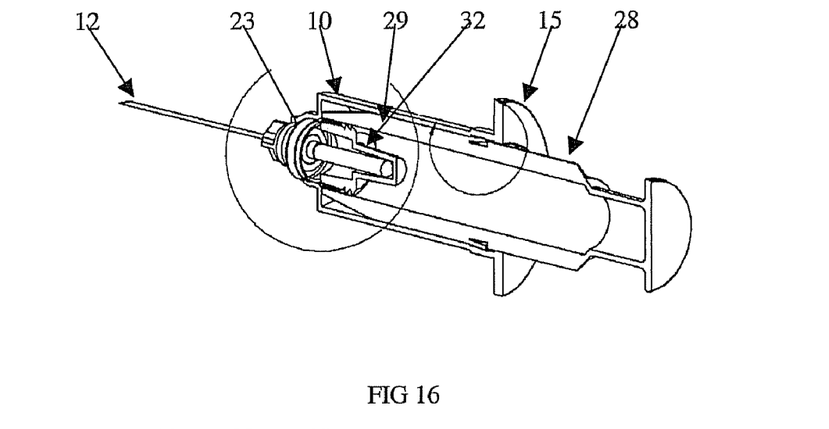
FIG. 16 illustrates a section view of the needle retraction device in the fully forward position.
Figure 17:
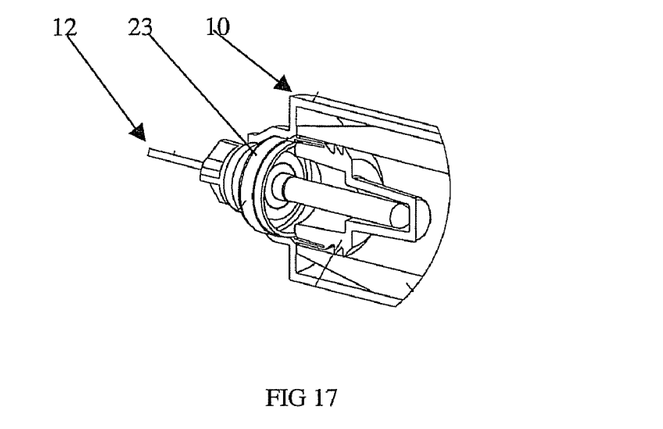
FIG. 17 illustrates an enlarged section view of FIG. 16.

The front part of housing 10 is provided with an extending collar 16 which is described in greater detail in FIG. 14 and FIG. 15. Collar 16 has a first annular portion 17 which extends substantially at right angles from the front of housing 10. The first annular portion extends into a second annular portion 18 which tapers and which extends into a small third annular portion 19 which is again at right angles relative to the front of housing 10. The first annular portion 17 is provided with a small internal annular groove 20 which forms part of the engagement means to engage the needle holder 11 to collar 16.

Needle holder 11 in the particular embodiment is formed in two parts being a larger internal part 21 and a smaller external part 22. The internal part 21 contains a passageway to accommodate the steel needle 12. The external part 22 extends about the inner portion of internal part 21 and accommodates the engagement means that releasably attaches the entire needle assembly relative to collar 16. Specifically, external part 22 is provided with an annular flange 23 which is best illustrated in FIG. 15. Flange 23 extends against the inside wall of first portion 17 and part of second portion 18. Flange 23 is manufactured to have a bias to press against the inside wall of collar 16. The portion of flange 23 that presses against the inside wall of first portion 17 is provided with a small extending rib 24 that engages into the groove 20 which is on first portion 17. Thus, this arrangement holds the needle holder against collar 16. Flange 23 however also terminates into a small angled lip 25 which projects slightly away from the junction of collar 16 and the remainder of housing 10 to provide a very small but significant gap, and this arrangement is to facilitate decoupling of the needle holder from the housing by the needle retraction device and this will be described in greater detail below.

Thus, as long as flange 23 is not interfered with or manipulated, it causes the needle holder 11 remain attached to collar 16.

With this arrangement, a blood collection chamber 13 (see FIG. 9) can be pushed into housing and against the inner part of needle 12 and upon further pushing (see FIG. 10) the inner part of the needle pierces the plug 14 of chamber 13 to expose the needle to the partial vacuum inside the chamber. The partial vacuum causes blood to be sucked through the needle and into the chamber. Once the chamber is sealed or has a desired quantity of blood, it can be simply pulled out of housing 10. Sometimes, a plurality of such chambers is used to provide a greater volume of blood.

Figure 11:
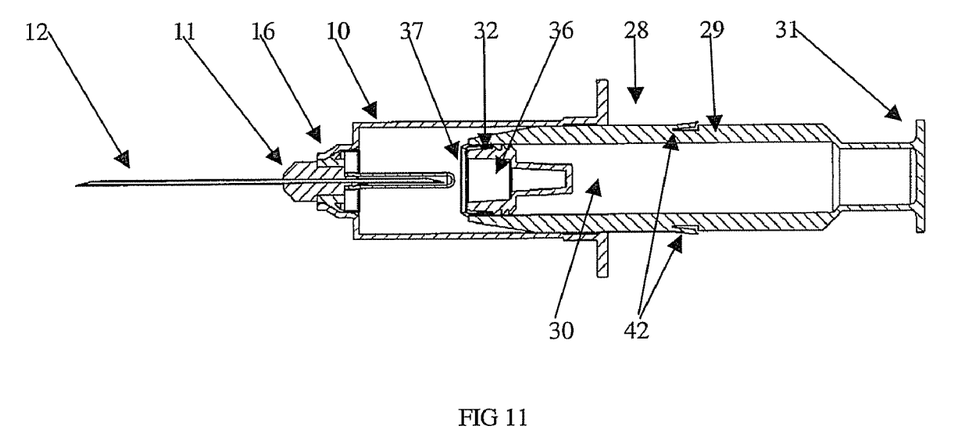
FIG. 11 illustrates a needle retraction device which is a separate member and which has been partially pushed into the housing.
Figure 12:
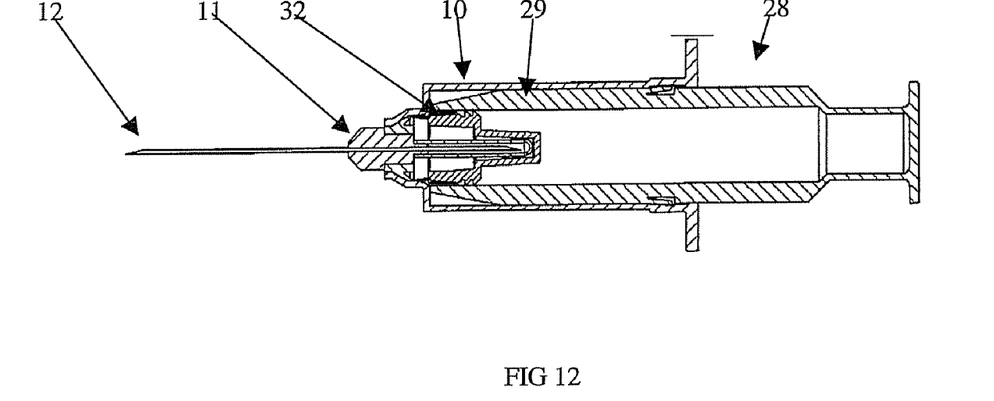
FIG. 12 illustrates the device of FIG. 11 now having been pushed into the fully forward position to couple against the needle holder and to release the needle holder from attachment to the housing.
Figure 13:
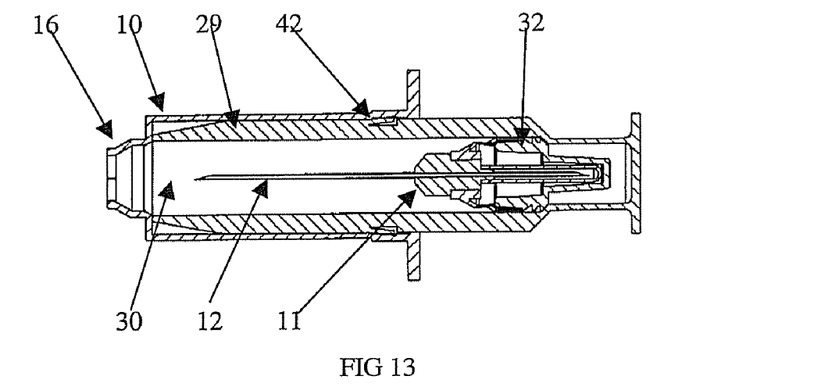
FIG. 13 illustrates the contaminated needle and needle holder, and the plug which forms part of the needle retraction device being sucked back into the needle retraction device to protect against needlestick injury.

Once all the blood has been collected, the next step of the present invention is to enable the needle to be retracted to prevent needlestick injury. This requires a separate device being the needle retraction device 28 and this device is illustrated in FIGS. 11-13. Basically, the needle retraction device 28 comprises an elongate body 29 which has a partially evacuated chamber 30. The rear part of device 28 is provided with a thumb or palm depressible portion 31 to facilitate pushing of the device into housing 10. The front of chamber 30 is open but is sealed with a plug 32. Plug 32 is designed to enable it to be sucked back into chamber 30 but in a sealing manner and therefore the outer wall of plug 32 contains annular sealing ribs 33 (see FIG. 15). This is not dissimilar to the plunger of a syringe. Plug 32 is however prevented from being sucked back into the partially evacuated chamber 30 by being releasably locked onto body 29. Specifically, and best illustrated in FIG. 14, plug 32 is provided with an annular flange 34 which is resilient but which is naturally biased against the inside wall of body 29. The outermost edge of annular flange 34 is provided with an abutment 35 which is generally "arrow" shaped, and has a face which abuts against the front edge of body 29 and therefore locks the plug against body 29 against being sucked back into the evacuated chamber 30. Therefore, as long as abutment 35 engages with the front edge of body 29, the plug can not be sucked back into the chamber.

Plug 32 is provided with its own internal chamber 36 the function of which is to accommodate the inner part of needle 12, this being best illustrated in FIG. 11. A small sealing membrane 37 is provided over the front of plug 32 and which can be pierced by the inner end of needle 12. The internal chamber 36 of plug 32 is not evacuated and the sealing membrane 37 is there to provide a clean finish and to prevent debris from passing into the chamber.

When the needle retraction device 28 is inserted into housing 10 and pushed all away to the end of housing 10, the contaminated needle and needle holder are sucked back into chamber 30 as follows: firstly, and particularly referring to FIG. 14 and FIG. 15, as the front of body 29 comes up against the inner end of housing 10, the abutment 35 on the edge of annular flange 34 begins to contact the inner edge between first portion 17 and the remainder of housing 10, and this inner edge 40 is ramped (this being best illustrated in FIG. 14 and FIG. 15). Moreover, the shape of abutment 35 is such that further forward movement of body 29 causes the abutment to ride along the ramped inner edge 40 and to be pressed inwardly. As the abutment is pressed inwardly, it becomes released from engagement with body 29 and therefore plug 32 becomes released from body 29. At the same time, the inward movement of abutment 35 causes the abutment to engage with the small lip 25 which is on the free end of annular flange 23 which forms part of the needle holder 11. Moreover, as well as engaging with the small lip 25, the inward movement also causes the annular flange 23 to move inwardly and this releases the small rib 24 from engagement with groove 20. Thus, the needle holder has now been decoupled or released from engagement with the housing, as well as the plug 32 becoming released or decoupled from body 29. The vacuum inside chamber 30 now causes plug 32 to be sucked back into the chamber, and as the plug is now coupled to the needle holder, the needle holder is also sucked back into the chamber. This final position is illustrated in FIG. 13. When the needle holder (containing the contaminated needle) is sucked back into the chamber, and as illustrated in FIG. 13, the needle is completely shielded by body 29.

Figure 18:
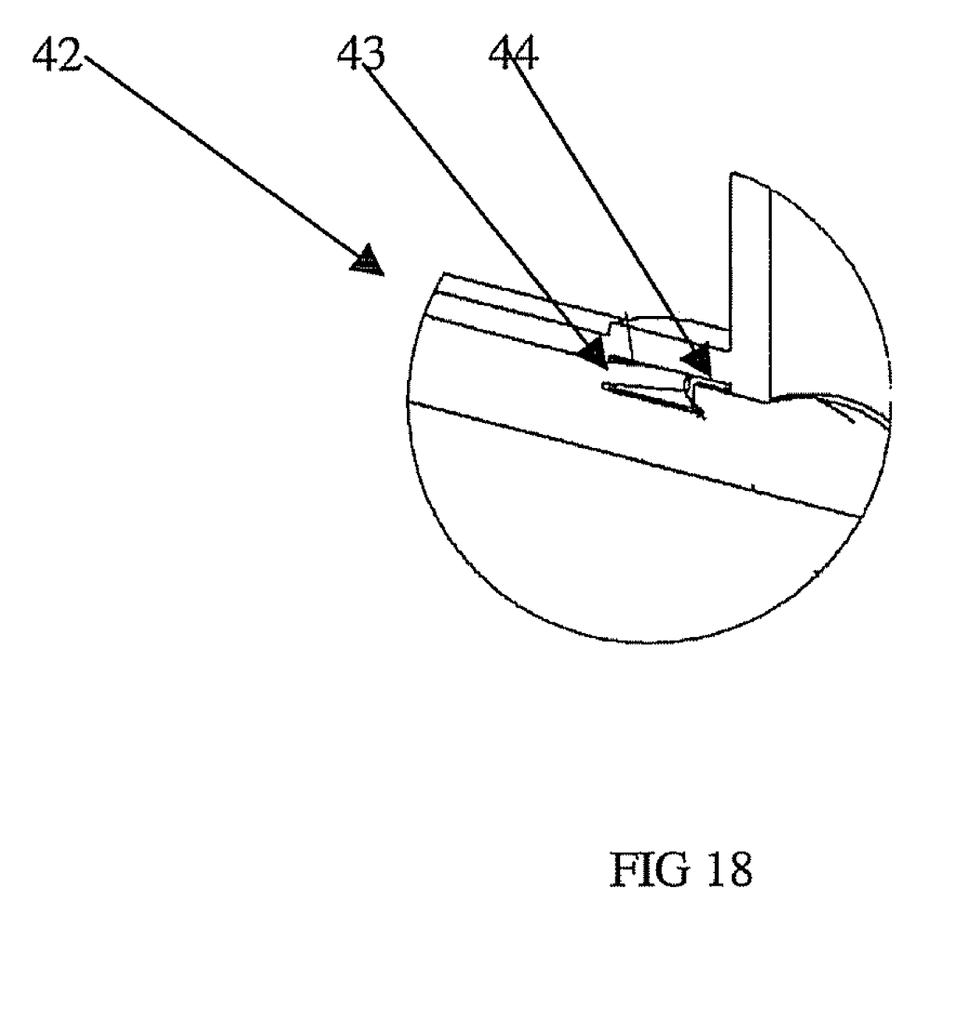
FIG. 18 illustrates a locking device to lock the needle retraction device against the housing.

However, to provide even further security, it is preferred that the needle retraction device 28 is locked against housing 10 once it has achieved a position of FIG. 12 or FIG. 13 and thus the needle retraction device 28 cannot be removed. This can be achieved by a small locking arrangement 42 which is best illustrated in FIG. 18. The locking arrangement comprises a small outwardly biased rib 43 which forms part of body 29 and which engages in a small slot 44 which forms part of housing 10. Thus, as the needle retraction device 28 is pushed fully into housing 10 (see FIG. 12 and FIG. 13), rib 43 springs outwardly into engagement with slot 44 and the needle retraction device cannot be retracted back out of housing 10.

Referring now to the first embodiment of the invention illustrated in FIGS. 1-8, there is illustrated a blood collection device that operates on the same principle as described in the second embodiment, but contains some different features.

Figure 4:
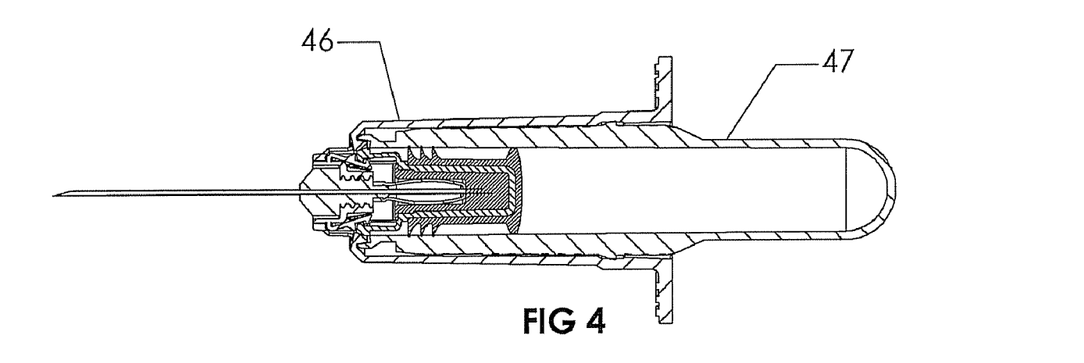
FIG. 4 illustrates the device of FIG. 3 now having been pushed into the fully forward position to couple against the needle holder and to release the needle holder from attachment to the housing.
Figure 5:
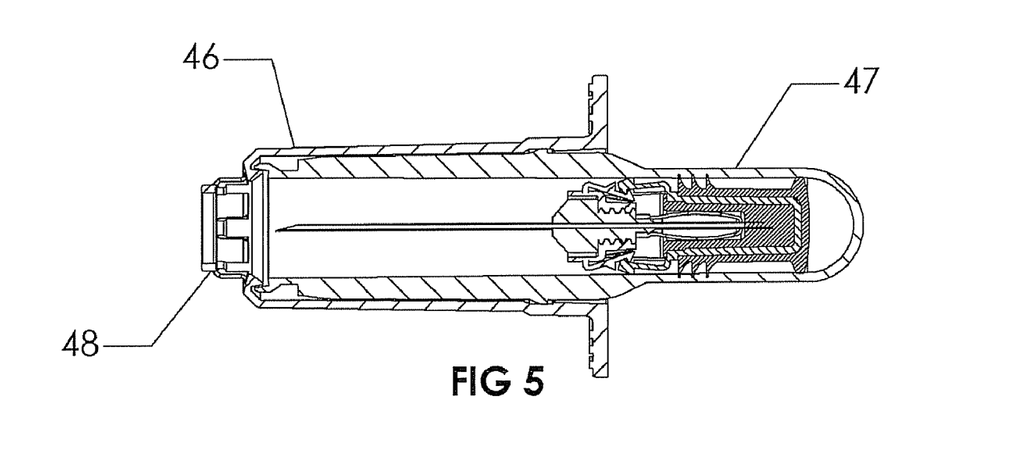
FIG. 5 illustrates the contaminated needle and needle holder, and the piston which forms part of the needle retraction device being sucked back into the needle retraction device to protect against needlestick injury.
Figure 6A:
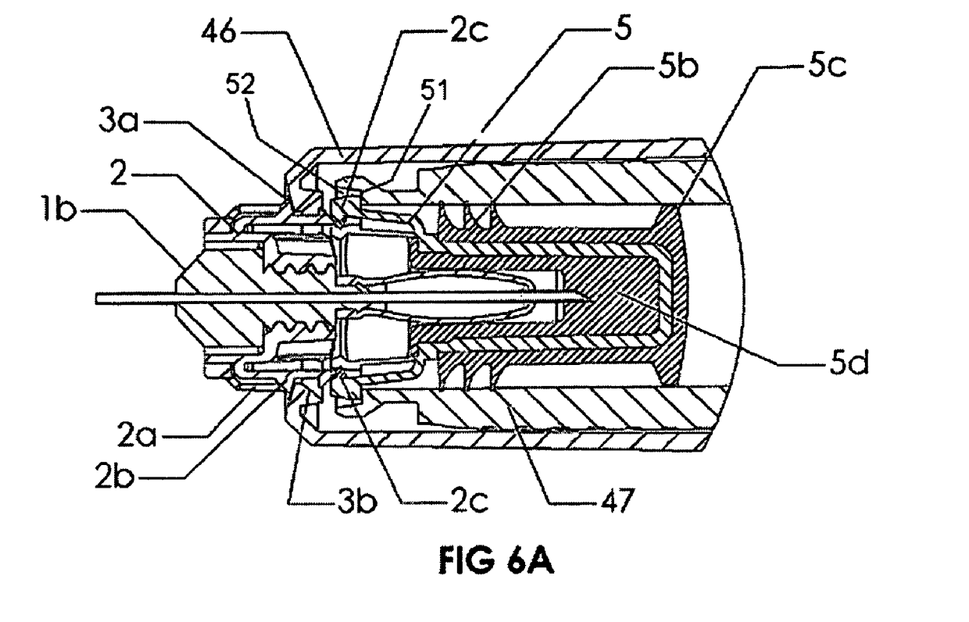
FIG. 6A illustrates in greater detail the position where the needle retraction device is just about to "trigger".
Figure 6B:
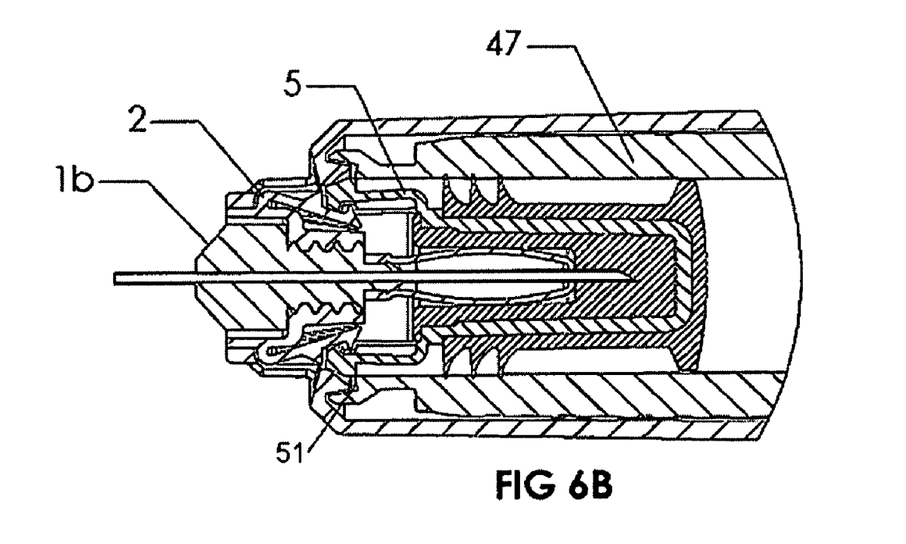
FIG. 6B illustrates in greater detail the position where the needle retraction device of FIG. 6A has been pushed a little further to show the various couplings and decouplings.
Figure 7A:
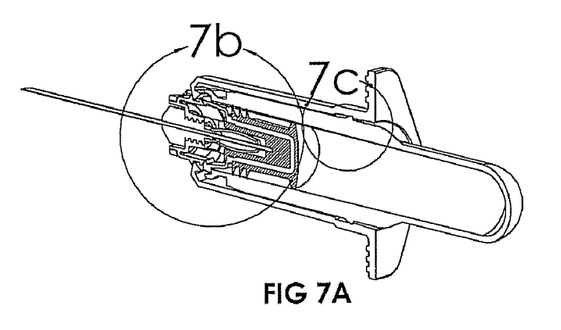
FIGS. 7A-C illustrate different section views of the first embodiment of the invention.
Figure 7B:
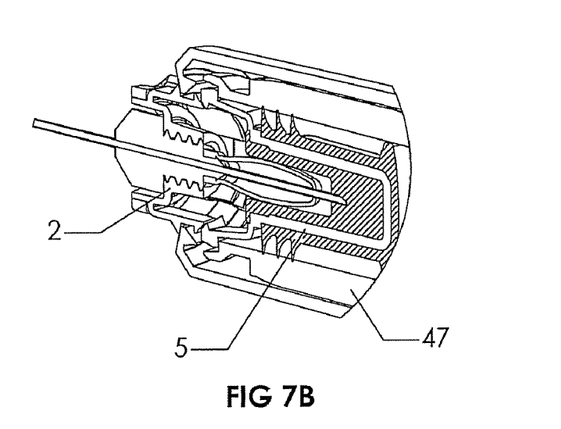
Figure 7C:
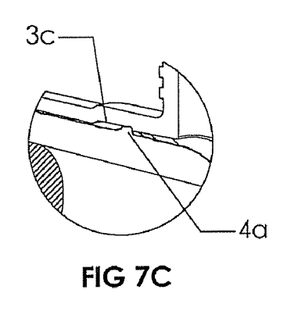
Figure 8:
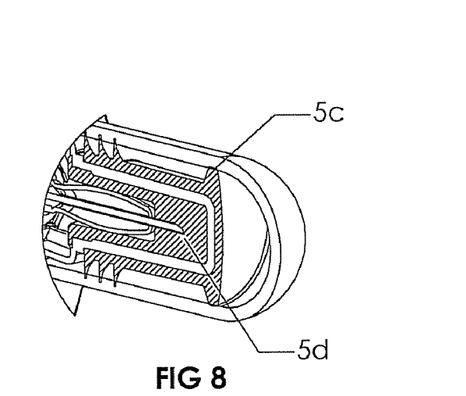
FIG. 8 illustrates in greater detail the piston and especially the piston brake that controls the retraction speed of the piston.

The general operation is illustrated in FIGS. 1-5, while FIGS. 6-8 illustrate in greater detail the particular features of the first embodiment.

Figure 1:
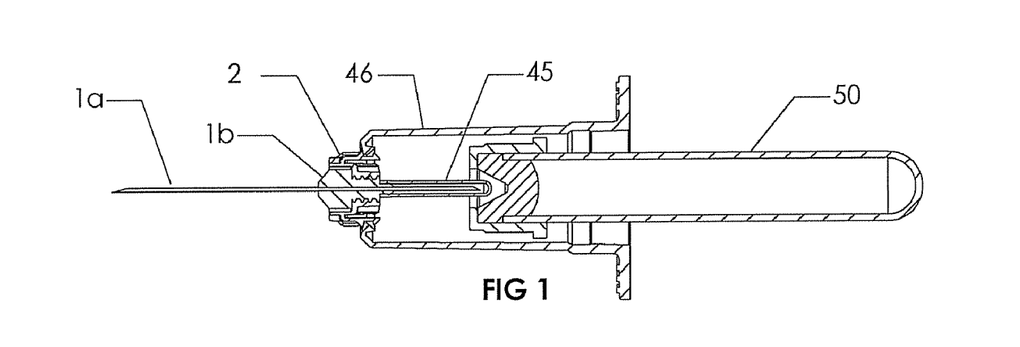
FIG. 1 illustrates a blood collection device according to a first embodiment of the invention together with a conventional blood collecting chamber which is partially pushed into the housing.

Specifically, FIG. 1 illustrates a housing 46 having an open rear end through which a conventional evacuated blood collection container 2 can pass, this container being similar to that illustrated in the second embodiment. The front of housing 46 contains a needle holder assembly, which in this particular embodiment comprises two separate parts being an inner needle holder 1B and an outer nosepiece 2 (see FIG. 6A).

A double ended steel puncture needle 1A extends through the inner needle holder 1B and into the interior of housing 46, this being not dissimilar to that described with reference to the second embodiment. The part of the puncture needle 1A that extends in housing 46 is covered by a protective flexible sheath 45 to keep the needle sterile until just before use.

FIG. 1 illustrates the blood collection container 50 pushed into the open rear end of housing 46 and almost in engagement with the rear of needle 1A.

Figure 2:
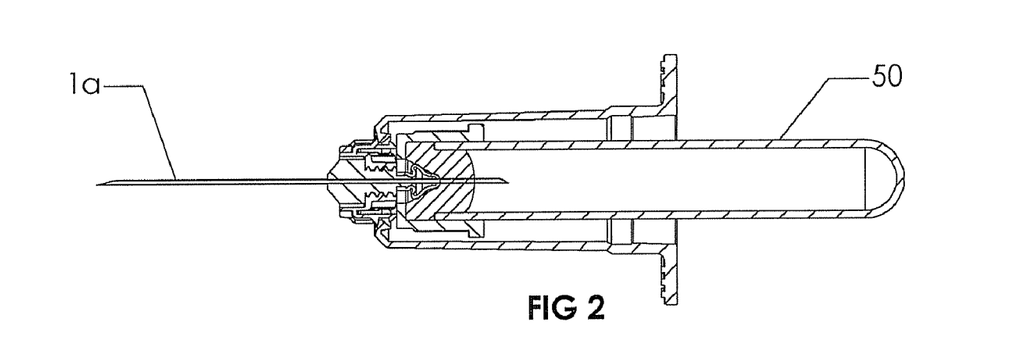
FIG. 2 illustrates the device of FIG. 1 but this time with the conventional blood collecting chamber being pushed fully into the housing to enable blood to be sucked into the chamber.

FIG. 2 illustrates further forward movement of the blood collection container 50 which has now been pushed against needle 1A with sufficient force to cause needle 1A to pass through the sealing bung on the forward end of container 50. The vacuum within container 50 will now cause blood or other body fluid to be sucked through needle 1A and into container 50. The arrangement also causes the protective sheath 45 to be pushed away to expose needle 1A, and this protective sheath is accommodated within an enlargement in the bung, this being illustrated in FIG. 2.

Figure 3:
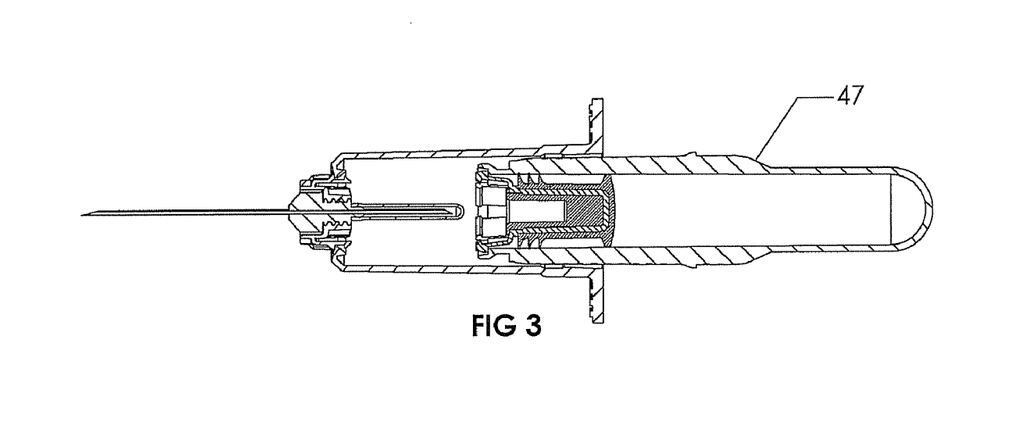
FIG. 3 illustrates a needle retraction device which is a separate member and which has been partially pushed into the housing.

FIGS. 3-5 illustrate a needle retraction device 47 in operation. The needle retraction device 47 is a separate member that is pushed into the rear of housing 46 after the blood collection container 50 has been filled and removed from the housing 46.

The needle retraction device 47 is somewhat similar to that described in the second embodiment and again comprises an elongate body which is hollow and which is under vacuum. The front of device 47 contains a piston assembly that can be coupled with the nosepiece 2 to retract the nosepiece and therefore the attached needle 1A back into the safety of the interior of the needle retraction device 47.

Thus, in FIG. 3, the needle retraction device 47 has been inserted into housing 46 and is being pushed forwardly towards the contaminated needle 1A.

In FIG. 4, the needle retraction device 47 has been pushed against the rear of the nosepiece 2 and is in the process of decoupling the nosepiece from the front of housing 46 (as will be described in greater detail below).

In FIG. 5, the needle retraction device has retracted the nosepiece containing the attached needle holder 1B and the attached needle 1A back into the interior of the device by the action of the vacuum in the device as will be described in greater detail below.

Referring now to FIG. 6A, this shows in greater detail the decoupling action and particularly illustrates the front of the needle retraction device 47 just before the point where the needle retraction device 47 decouples nosepiece 2.

Specifically, housing 46 is moulded with an internal ramp 3B to assist in the decoupling process. The front of housing 46 contains a smaller head portion 48 (see FIG. 5) to contain at least part of nosepiece 2, the needle holder 1B, and the attached puncture needle 1A.

The needle holding assembly basically comprises three parts being the nosepiece 2, the needle holder 1B, and the puncture needle 1A.

Nosepiece 2 is an outer member and is substantially hollow to accommodate the needle holder 1B which sits substantially inside nosepiece 2. The needle holder 1B, contains a conventional internal passageway to accommodate the puncture needle 1A.

Nosepiece 2 contains a plurality of retaining claws 2B that comprise finger members which are provided with "arrowhead" shaped portions, one portion being on the end of the finger member, and the other portion being positioned intermediate the length of the finger portion.

As illustrated in FIG. 6B, the intermediate arrowhead shaped portion abuts against the rear of ramp 3B which forms part of housing 46, and the arrangement prevents the needle holding assembly from being retracted into the housing.

To prevent the needle holding assembly from being pulled out the front of the housing, there is provided a nosepiece retraining groove 3A in housing 46 into which the intermediate arrowhead shaped portion passes. Thus, the intermediate arrow shaped head portion functions to hold the nosepiece, and therefore the entire needle holding assembly from being pushed into housing 46 and from being pulled out of the front of housing 46. An anti-spin key 2A is also provided.

Therefore, until the retaining claw 2B (which contains the intermediate arrow shaped portion) is moved, the needle holding assembly is locked in place.

The front of the needle retraction device 47 is open but is closed by a piston assembly having a particular configuration. Referring to FIG. 6A, the piston assembly comprises a generally hollow cylindrical piston 5 made of solid (typically plastic) material. Piston 5 contains an outer rubber cover that contains a plurality of sealing rings 5B, the function of which is to keep a vacuum tight seal between the piston and the evacuated main body of the needle retraction device 47.

The outer rubber cover also contains a further outwardly extending ring 5C that grips the inside wall of the needle retraction device and which functions to act as a "brake" or a "speed controller" to control the retraction of the piston into the needle retraction device. To explain, without this additional part, retraction of the piston can be quite sudden and can cause alarm to the person using the device. The outwardly extending ring 5C functions to slow down the retraction of the piston by increasing the frictional grip of the piston against the inside wall of the needle retraction device.

As mentioned previously, piston 5 is generally hollow to accommodate the inner end of the (contaminated) puncture needle 1A and the protective sheath 45. However, the inside of piston 5 does contain some soft material 5D that may comprise rubber or something else and that can be pierced by the inner end of the puncture needle 1A. This is illustrated in FIG. 6A. Thus, before the needle retraction device is triggered to retract the needle back into the device (this being the position illustrated in FIG. 6A), the inner end of the puncture needle has passed into the soft material 5D which functions to plug the needle to prevent blood spray during the retraction process.

The front of piston 5 contains a plurality of withdrawal claws 2C. These claws comprise forwardly extending fingers that contain an arrowhead shaped projection at the end of each finger. It can be seen from FIG. 6A, that these withdrawal claws 2C are at least partially housed in recess 52 in the inner surface of the needle retraction device 47. Additionally, withdrawal claws 2C engage against a shoulder 51 created by recess 52 in the front of the needle retraction device 47 and therefore lock the piston against retraction into the needle retraction device. Thus, until these withdrawal claws are moved, the piston is locked against retraction.

Just prior to triggering, the needle retraction device is in the position illustrated in FIG. 6A where the withdrawal claws 2C are just touching the retaining claws 2B which are on nosepiece 2.

Referring now to FIG. 6B, this illustrates the point of triggering where the piston has been decoupled from the needle retraction device and can now be sucked back by the vacuum in the needle retraction device, and the nosepiece has been decoupled from the front of housing 46 and has been attached to piston 5 such that retraction of the piston also causes retraction of the nosepiece and thus the attached contaminated puncture needle 1A.

As the needle retraction device is pushed slightly more into the housing 46, the withdrawal claws 2C engage against the arrowhead projection on the end of each retaining claw 2B and start to push the retaining claw inwardly. This action causes the intermediate projection on the retaining claw 2B to disengage against abutment against the housing 46, and also causes the intermediate projection to exit the nosepiece retaining groove 3A. Thus, the nosepiece 2 becomes free from engagement against housing 46.

However, at the same time the withdrawal claws 2C lock against the retaining claws 2B such that the nosepiece 2 now becomes locked to piston 5. This position is illustrated in FIG. 6B.

At or about the same time, the withdrawal claws 2C on the piston ride up the ramp 3B which forms part of housing 46 and in doing so, the claws are pushed inwardly and therefore no longer engage with the front of the needle retraction device 47. Ramp 3B also functions to ensure that the withdrawal claws 2C are properly locked against the retaining claws 2B.

Thus, the arrangement is that piston 5 becomes freed from the needle retraction device 47, nosepiece 2 becomes freed from engagement against housing 46, and the piston 5 locks against nosepiece 2.

The vacuum within the needle retraction device 47 now functions to suck back the piston 5 into the rear of the device, this being best illustrated in FIG. 5. The contaminated needle is now perfectly safe.

Referring to FIGS. 7A-C, there is illustrated a locking arrangement to temporarily lock the vacuum tube (blood collection container 2) to the housing 46. The housing 46 contains a locking groove 3C, that accommodates a locking claw or projection 4A on the outside wall of the vacuum tube.

Throughout the specification and the claims (if present), unless the context requires otherwise, the term "comprise", or variations such as "comprises" or "comprising", will be understood to apply the inclusion of the stated integer or group of integers but not the exclusion of any other integer or group of integers.

Throughout the specification and claims (if present), unless the context requires otherwise, the term "substantially" or "about" will be understood to not be limited to the value for the range qualified by the terms.

It should be appreciated that various other changes and modifications can be made to any embodiment described without departing from the spirit and scope of the invention.

The invention claimed is:

1. A blood collection device comprising:
a housing having an open rear end adapted to accommodate an evacuated blood collecting tube, and a front end;
a needle holder in the front end;
a needle which is attached to the needle holder and has a first end that projects from the housing and a second end that projects into the housing, the needle holder being releasably attached relative to the housing to enable the needle holder and the attached needle to be retracted; and
a needle retraction device, the needle retraction device able to be pushed into the housing, the needle retraction device comprising at least two engagement means adapted to release the needle holder from the housing and to respond to a retraction bias to retract the needle holder the attached needle into the needle retraction device,
wherein
the needle holder includes an annular ring with at least two finger members extending therefrom that engage relative to the housing to retain the needle holder to the housing, each finger member being deflectable between a locking position where the finger member retains the needle holder to the housing, and a release position where the needle holder can be retracted into the housing, and
each of the at least two engagement means is at least partially housed in abutment with a shoulder of a recess defined within an inner surface of the needle retraction device in opposition to the retraction bias prior to the release of the needle holder from the housing.

2. The device as claimed in claim 1, wherein the needle holder comprises first part being an inner part and containing a passageway through which a puncture needle can extend to fit the puncture needle to the inner part, a second part comprising an outer nosepiece, the at least two finger members being attached relative to the outer nosepiece.

3. The device as claimed in claim 2, wherein the needle retraction device comprises an elongate hollow body which contains a vacuum and which has an open end, a piston which closes off the open end of the elongate hollow body and which is adapted for sliding movement within the elongate hollow body, and which is releasably attached relative to the open end.

4. The device as claimed in claim 3, further comprising at least two finger members on the piston which releasably attach the piston relative to the open end of the hollow body, each finger member of the piston being movable between a locking position where the piston is attached to the elongate hollow body, and a release position where the piston can be retracted into the hollow elongate body under the influence of the vacuum.

5. The device as claimed in claim 4, wherein the at least two finger members on the piston extend forwardly from the piston, and the at least two finger members on the needle holder extend rearwardly such that as the needle retraction device is pushed against the rear of the needle holder, the at least two finger members on the piston release the at least two finger members on the needle holder, and engage to the at least two finger members on the needle holder.

6. The device as claimed in claim 5, wherein the housing is provided with a ramp in a forward portion of the housing, the ramp contacting the at least two finger members on the piston when the needle retraction device is pushed against the rear of the needle holder, the at least two finger members riding along the ramp to release the at least two finger members from engagement with the elongate hollow body to enable the piston containing the attached needle holder to be retracted into the elongate hollow body under the influence of vacuum.

7. The device as claimed in claim 6, wherein the piston contains a pierceable material that is pierced by the second end of the needle when the needle retraction device is pushed against the rear of the needle holder to seal the inner end of the needle.

8. The device as claimed in claim 7, wherein the piston contains a speed controller to control a speed of retraction of the piston into the elongate hollow body, the speed controller comprising a sealing member extending from the piston and sealingly engaging with the elongate hollow body to increase the frictional force of the piston on the elongate hollow body.

9. The device as claimed in claim 1, wherein the at least two finger members are radially spaced about the needle holder.

* * * * *